(12) United States Patent
Qian et al.

(10) Patent No.: US 10,261,133 B2
(45) Date of Patent: Apr. 16, 2019

(54) BATTERY TESTING APPARATUS

(71) Applicants: Tsinghua University, Beijing (CN);
HON HAI PRECISION INDUSTRY CO., LTD., New Taipei (TW)

(72) Inventors: Li Qian, Beijing (CN); Yu-Quan Wang, Beijing (CN); Fu-Jun Wang, Beijing (CN); Li-Yong Ma, Beijing (CN); Xue-Wei Guo, Beijing (CN); Yang Wu, Beijing (CN)

(73) Assignees: Tsinghua University, Beijing (CN);
HON HAI PRECISION INDUSTRY CO., LTD., New Taipei (TW)

( * ) Notice: Subject to any disclaimer, the term of this patent is extended or adjusted under 35 U.S.C. 154(b) by 23 days.

(21) Appl. No.: 15/702,864

(22) Filed: Sep. 13, 2017

(65) Prior Publication Data

US 2018/0210035 A1 Jul. 26, 2018

(30) Foreign Application Priority Data

Jan. 23, 2017 (CN) .......................... 2017 1 0058186

(51) Int. Cl.
*G01R 31/36* (2006.01)
*G01N 21/27* (2006.01)
*H01M 10/42* (2006.01)

(52) U.S. Cl.
CPC ......... *G01R 31/3644* (2013.01); *G01N 21/27* (2013.01); *G01R 31/3627* (2013.01); *H01M 10/4285* (2013.01)

(58) Field of Classification Search
CPC .................................................. G01R 31/3644
See application file for complete search history.

(56) References Cited

U.S. PATENT DOCUMENTS

2010/0054488 A1* 3/2010 Young .................... H04R 29/00
381/60

* cited by examiner

*Primary Examiner* — Clayton E. LaBalle
*Assistant Examiner* — Jas A Sanghera
(74) *Attorney, Agent, or Firm* — ScienBiziP, P.C.

(57) ABSTRACT

The disclosure relates to a battery testing apparatus. The battery testing apparatus includes a substrate and a body, the body is located on the substrate. The body includes a bottom, a central body and a cover, the bottom, the central and the cover is electrically insulated from each other. The substrate defines a first electrode point, a second electrode point and a third electrode point, the three electrode points are insulated from each other, the first electrode point is electrically connected with the central body, the second electrode point is electrically connected with the bottom, the third electrode point is electrically connected with the cover. The battery testing apparatus is configured to test electrochemical performance of a battery by a three-electrode method.

12 Claims, 7 Drawing Sheets

BATTERY TESTING APPARATUS

CROSS-REFERENCE TO RELTATED APPLICATIONS

This application claims all benefits accruing under 35 U.S.C. § 119 from China Patent Application No. 201710058186.X, filed to Jan. 23, 2017, in the China Intellectual Property Office, the disclosure of which is incorporated herein by reference.

FIELD

The subject matter herein generally relates to a battery testing apparatus, particularly, to the battery testing apparatus for testing electrochemical battery.

BACKGROUND

A conventional battery testing apparatus is configured to test the electrochemical property of batteries, such as lithium-ion battery, air battery. However, the conventional battery testing apparatus has many elements, which make the battery testing apparatus larger and thicker. Therefore the conventional battery testing apparatus is not easy to assemble or disassemble. Further, it is inconvenient to use the battery testing apparatus.

What is needed, therefore, is to provide a battery testing apparatus which can overcome the shortcomings as described above.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

DETAILED DESCRIPTION

Figure 1:
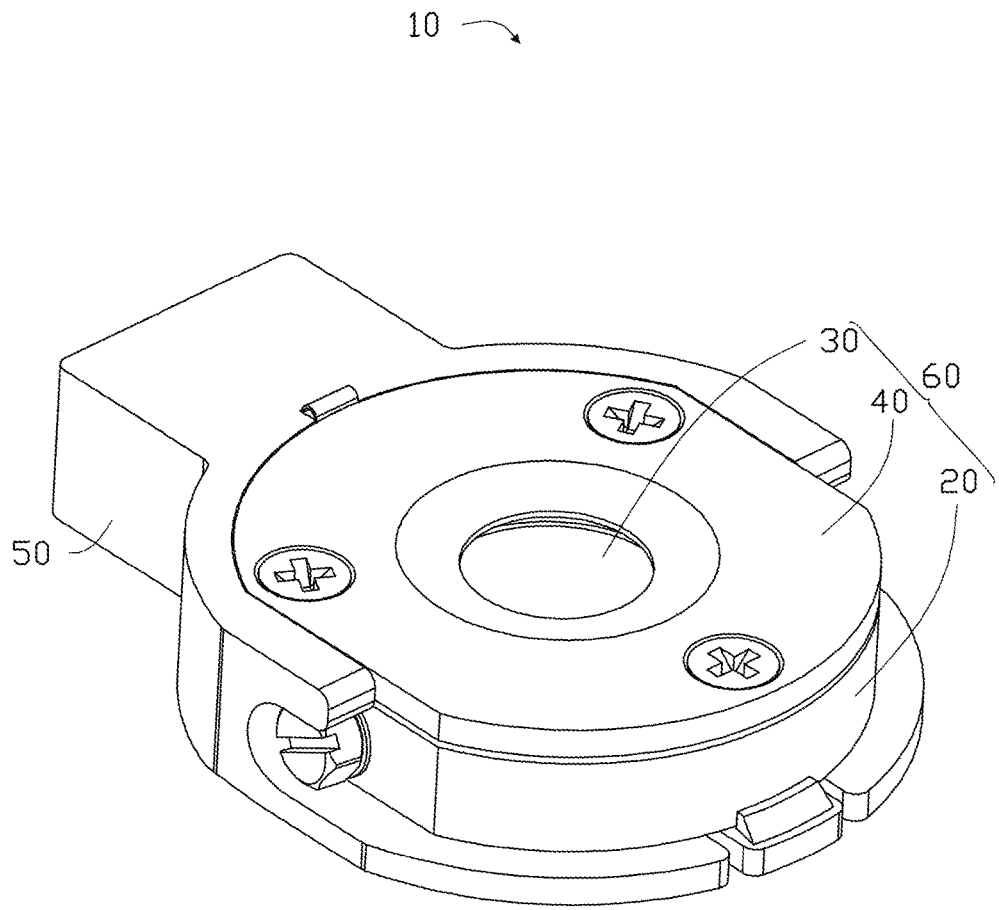
FIG. 1 is a schematic view of one embodiment of a battery testing apparatus.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The connection can be such that the objects are permanently connected or releasably connected. The term "substantially" is defined to be essentially conforming to the particular dimension, shape or other word that substantially modifies, such that the component need not be exact. The term "comprising" means "including, but not necessarily limited to"; it specifically indicates open-ended inclusion or membership in a so-described combination, group, series and the like. It should be noted that references to "an" or "one" embodiment in this disclosure are not necessarily to the same embodiment, and such references mean at least one.

The present disclosure relates to a battery testing apparatus described in detail as below.

Figure 2:
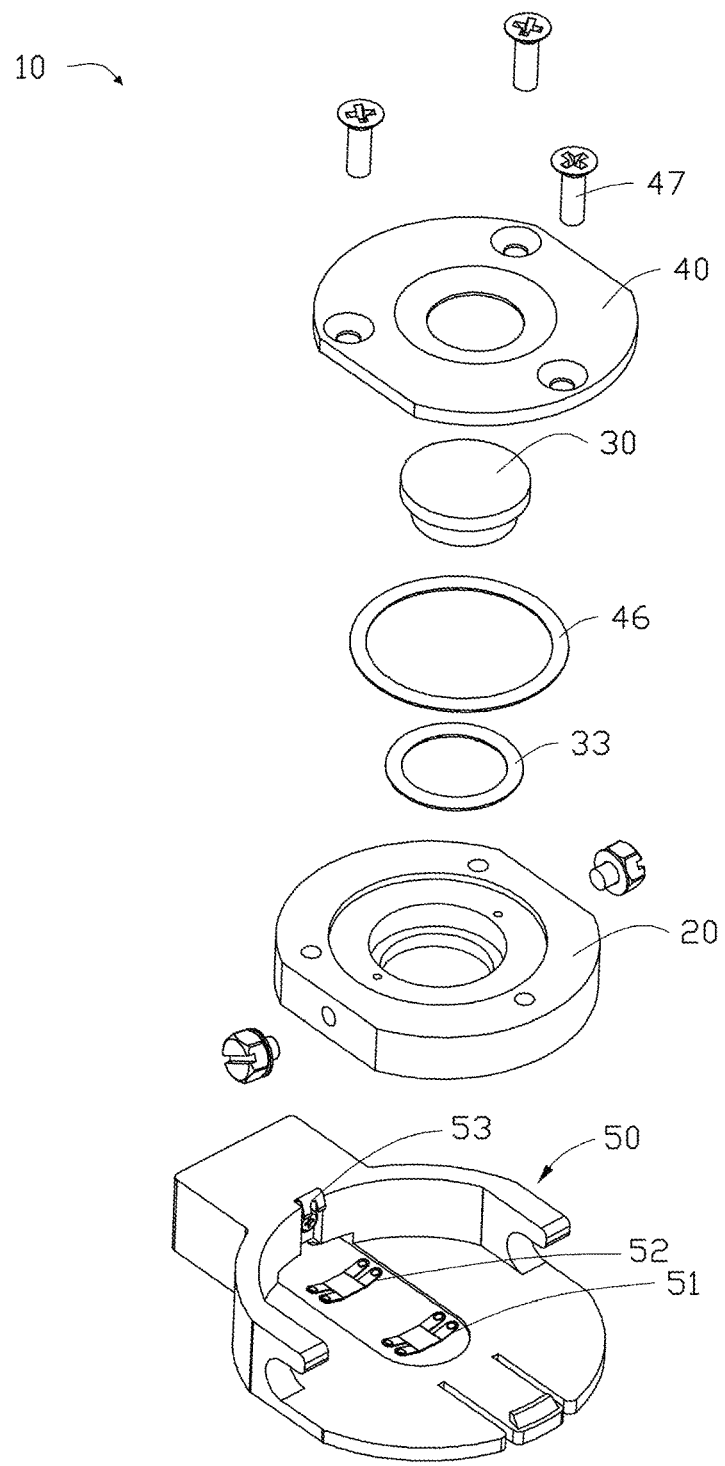
FIG. 2 is a exploded schematic view of the battery testing apparatus in FIG. 1.

Referring to FIG. 1 and FIG. 2, a battery testing apparatus 10 according to one embodiment is provided. The battery test apparatus 10 includes a substrate 50 and a body 60. The body 60 includes a bottom 20, a central body 30 and a cover 40.

Figure 3:
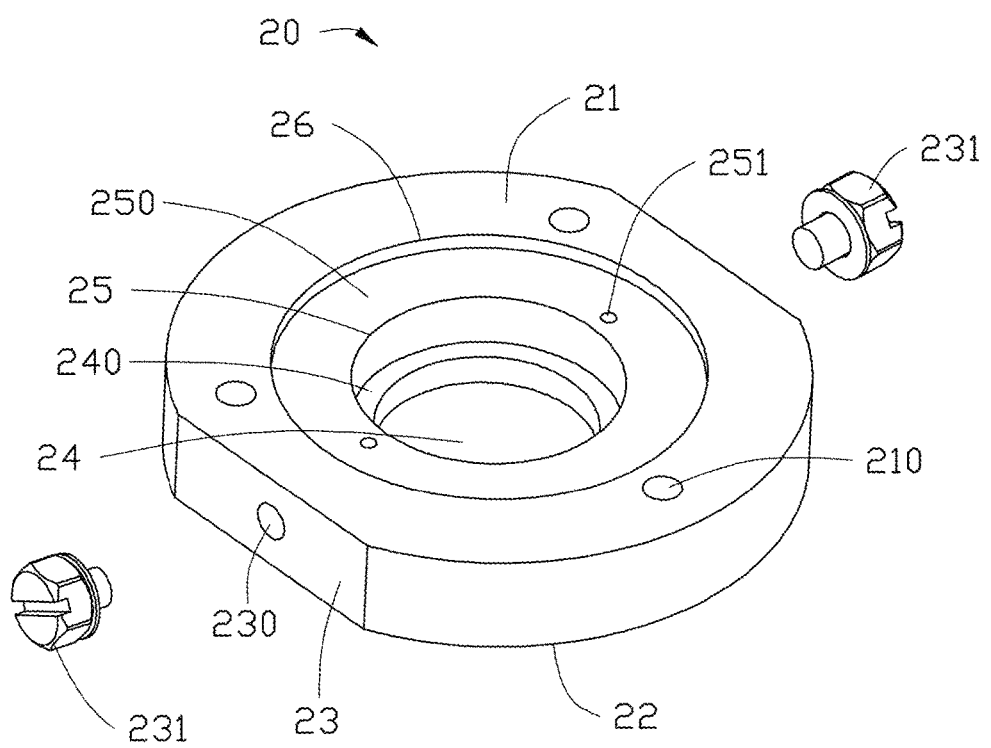
FIG. 3 is a schematic view of a bottom of the battery testing apparatus in FIG. 1.

Referring to FIG. 3, the bottom 20 defines a first top surface 21, a first bottom surface 22 and a first side surface 23. The first top surface 21 defines a plurality of screw holes 210. In one embodiment, the first top surface 21 defines three screw holes 210. The bottom 20 defines a first hole 24, a second hole 25 and a third hole 26, wherein the first hole 24, the second hole 25 and the third hole 26 gets through the first bottom surface 22 to the first top surface 21. A diameter of the first hole 24 is smaller than that of the second hole 25. A first step 240 is formed between the first hole 24 and the second hole 25. A diameter of the second hole 25 is smaller than that of the third hole 25. A second step 250 is formed between the second hole 25 and the third hole 26.

The side surface 23 defines two holes 230. The two holes 230 are opposite with each other. The bottom 20 includes two plugs 231. The two plugs 231 are inserted into the two holes 230. An amount of the plugs 231 is equal to an amount of the holes 230. In another embodiment, the bottom 20 can also include two gas pipes (not shown). The two gas pipes can be inserted into the two holes 230, and gas enters and discharges the battery testing apparatus 10 from the gas pipes. An amount of the gas pipes is equal to the amount of the holes 230.

The second step 250 defines two air holes 251. The two air holes 251 are opposite with each other. An extending direction of the air holes 251 is perpendicular to that of the holes 230. The two air holes 251 are respectively communicated with the two holes 230. An amount of the air holes 251 is equal to the amount of the holes 230.

Figure 4:
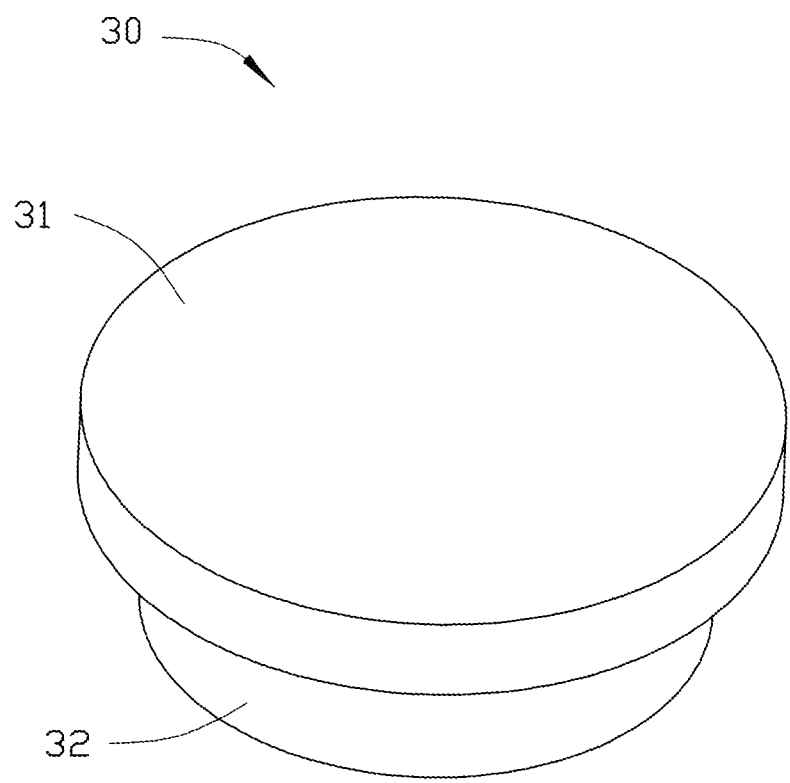
FIG. 4 is a schematic view of a central body of the battery testing apparatus in FIG. 1.

Referring to FIG. 4, the central body 30 has a pin structure and includes a head 31 and a column 32 extending downwardly from the head 31. A shape of the head is cylindrical structure. A diameter of the head 31 is greater than a diameter of the column 32. The diameter of the head 31 is smaller than the diameter of the second hole 25. The diameter of the column 32 is smaller than the diameter of the first hole 24. A height of the head 32 is smaller than a height of the second hole 25.

When the central body 30 is inserted into the bottom 20, the head 31 is located in the second hole 25 and the column 32 is located in the first hole 24. A first insulated washer 33 is located between the head 31 and the first step 240. The central body 30 is electrically insulated from the bottom 20.

Figure 5:
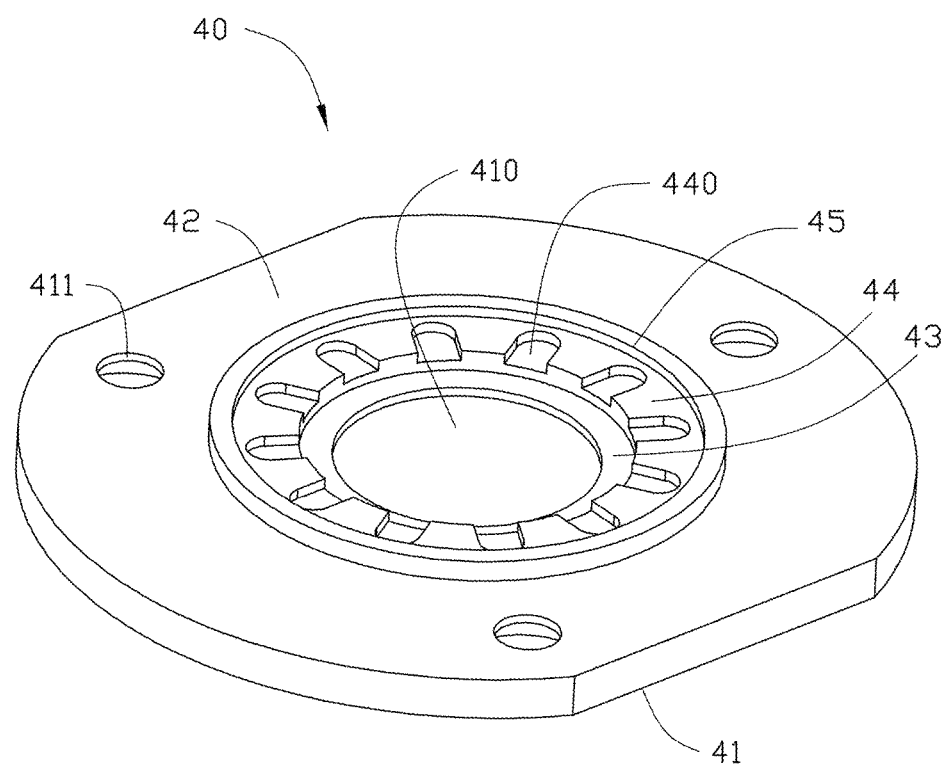
FIG. 5 is a schematic view of a cover of the battery testing apparatus in FIG. 1.

Referring to FIG. 5, center of the cover 40 defines a through hole 410, a side of the cover 40 defines a plurality of counter bores 411. An amount of the counter bores 411 is equal to an amount of the screw holes 210. In another embodiment, the cover 40 defines three counter bores 411. The cover 40, the central body 30 and the bottom 20 are fixed together by an insulated bolt 47. The insulated bolt 47 is inserted into the counter bores 411 and the screw holes 210.

The cover 40 defines a second top surface and a second bottom surface. The cover 40 includes three ring bosses. The three ring bosses includes a first ring boss 43, a second ring boss 44 and a third ring boss 45 from top surface to bottom surface. The three ring bosses are coaxial with the through hole 410. A height of the first ring boss 43 is smaller than a height of the second ring boss 44. The height of the second ring boss 44 is smaller than a height of the third ring boss 45. A diameter of the first ring boss 43 is smaller than a diameter of the second ring boss 44. The diameter of the second ring boss 44 is smaller than a diameter of the third ring boss 45. The diameter of the third ring boss 45 is smaller than the diameter of the third hole 26.

The second ring boss 44 defines a groove 440. An amount of the groove 440 is not limited, it can be one or more. In another embodiment, the groove 440 is one ring groove. When the cover 40 is assembled on the bottom 20, a second insulated washer 46 is located between the third ring boss 45 and the second step 250. The bottom 20, the central body 30 and the cover 40 is electrically insulated from each other.

The cover 40 further includes a quartz glass (not shown), the cover 40 defines a hollow space, the quartz glass is located in the hollow of the first ring boss, and seals the through hole 410. In another embodiment, the quartz glass can be regarded as a window, a light enters the battery test apparatus 10 through the window.

Figure 6:
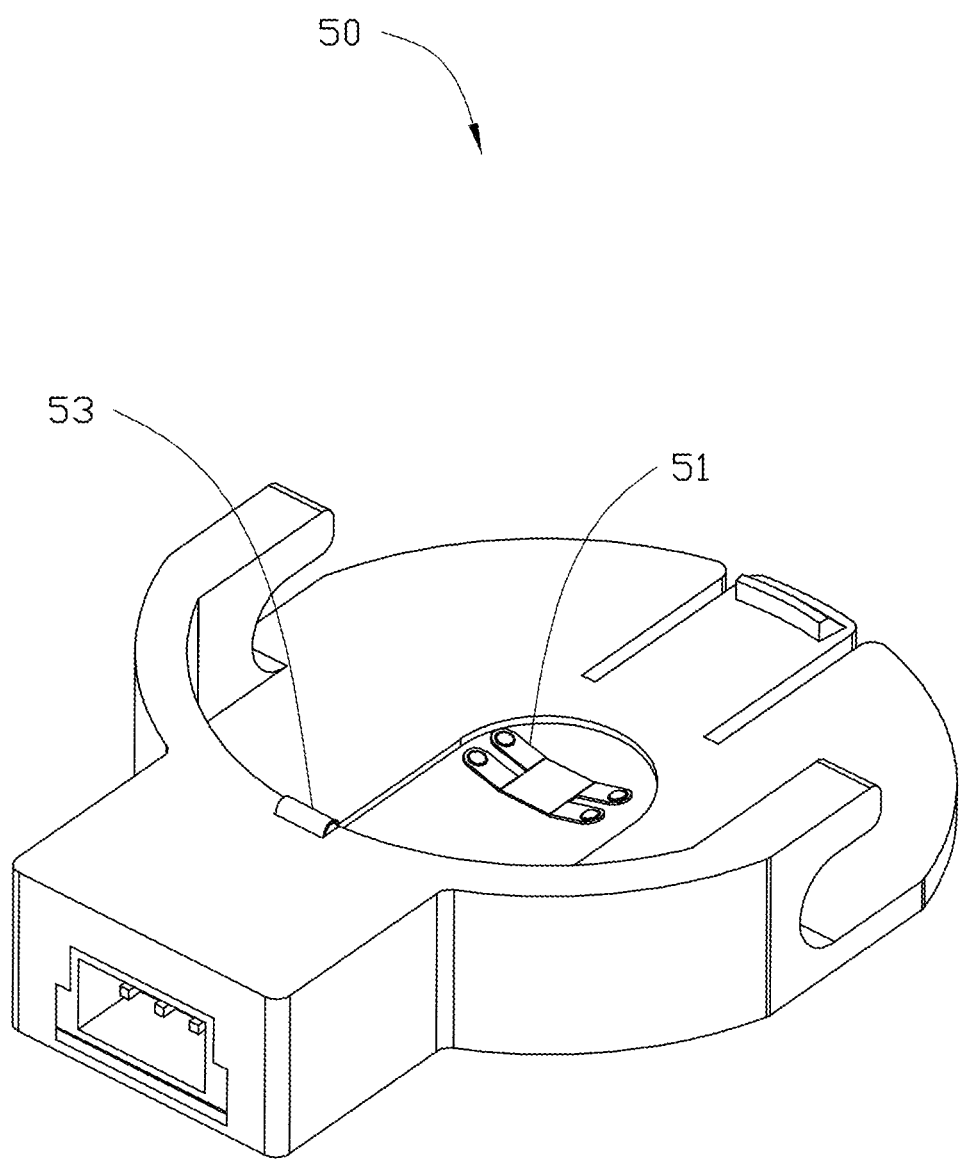
FIG. 6 is a schematic view of a substrate of the battery testing apparatus in FIG. 1.

Referring to FIG. 6, the substrate 50 defines three electrode points, that is, a first electrode point 51, a second electrode point 52 and a third electrode point 53. The three electrode points are insulated from each other. The three electrode points are electrically connected with three pins. The three pins are packaged to form a three-pin socket. When the body 60 is assembled on the substrate 50, the body 60 is fixed on the substrate 50 to make sure that elements of the body 60 is electrically connected with the three electrode points of the substrate 50. The body 60 is electrically connected with the first electrode point 51, the bottom 20 is electrically connected with the second electrode point 52, the cover 40 is electrically connected with the third electrode point 53. In another embodiment, the three electrode points can be electrically connected with three electrode lines.

Figure 7:
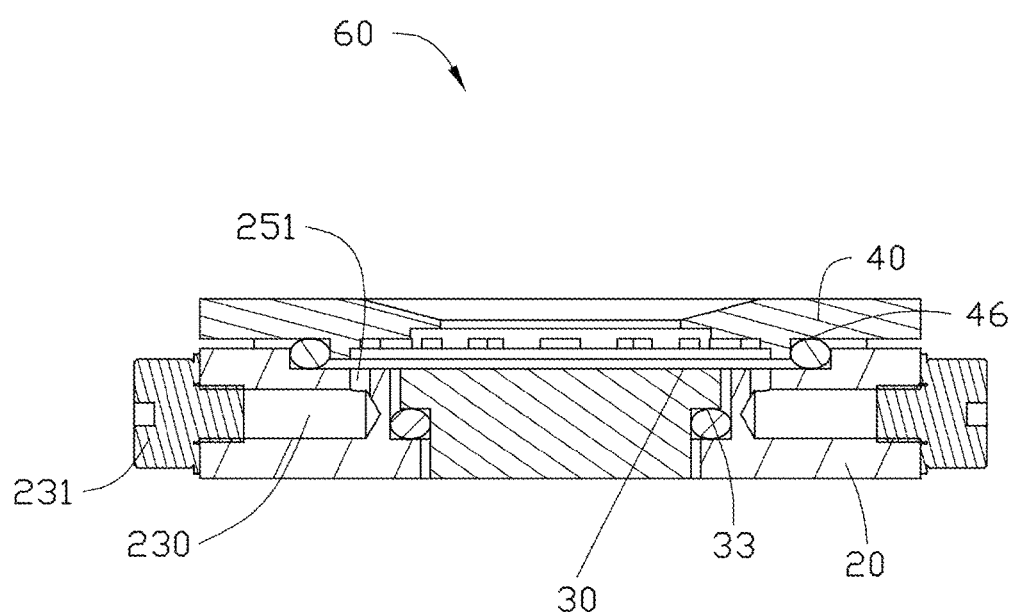
FIG. 7 is a cross sectional view of a body of the battery testing apparatus in FIG. 1.

Referring to FIG. 7, the battery test apparatus 10 is configured to test electrochemical performance of a battery by a three-electrode method. A type of the battery is not limited, it can be a lithium-ion battery or an air battery. When the battery is a lithium-ion battery, the two holes 230 and the two plugs 231 can be omitted from the bottom 20; and the two air holes 251 can be omitted from the second step 250; and the groove 440 or the ring groove can be omitted from the second ring boss 44.

In use of the battery testing apparatus 10, a three-electrode method is provided to test a battery. The battery includes a cathode and an anode. A reference electrode is further provided to form a three-electrode system with the cathode and the anode, in which the cathode is regarded as a working electrode, the anode is regarded as a assisting electrode. The working electrode and the reference electrode form an almost non-conducting system to measure the electrode potential of the working electrode by the potential stability of the reference electrode. The working electrode and the assisting electrode form a conducting system to measure a current through the working electrode.

In one embodiment, the battery testing apparatus 10 is used to test lithium-ion battery by the three-electrode method. First, a lithium-ion battery and a reference electrode are provided, wherein the lithium-ion battery includes a cathode, an anode and a diaphragm. The anode is located on a surface of the head 31 to make sure that the anode is electrically connected with the first electrode point 51. The reference electrode is located on a surface of the second step 250 to make sure that the reference electrode is electrically connected with the second electrode point 52. The diaphragm is located on the reference electrode, and the reference electrode is covered by the diaphragm. The cathode is located on a surface of the diaphragm. An area of the cathode is smaller than an area of the diaphragm. The cathode is in contact with the second ring boss 44 to make sure that the cathode is electrically connected with the third electrode point 53.

In another embodiment, a light is incident to the surface of the working electrode through the window and produce a reflected light, the reflected light is detected by a spectrometer, thus achieve on-line detection of the working electrode.

Depending on the embodiment, certain of the steps of methods described may be removed, others may be added, and the sequence of steps may be altered. The description and the claims drawn to a method may include some indication in reference to certain steps. However, the indication used is only to be viewed for identification purposes and not as a suggestion as to an order for the steps.

What is claimed is:
1. A battery testing apparatus comprising:
a substrate and a body, wherein the body is fixed on the substrate, the body comprises:
a bottom defining a first top surface, a first bottom surface and a first side surface, the bottom defines a first hole, a second hole and a third hole, wherein the first hole, the second hole and the third hole gets through the first bottom surface and the first top surface, a diameter of the first hole is smaller than a diameter of the second hole, whereby a first step is formed between the first hole and the second hole, the diameter of the second hole is smaller than a diameter of the third hole, whereby a second step is formed between the second hole and the third hole;
a central body comprising a head and a column connected with the head, the column is located in the first hole, and the head is located in the second hole;
a cover defining a second top surface and a second bottom surface, the cover defines a through hole, the cover further defines a first ring boss, a second ring boss and a third ring boss, wherein the first ring boss, the second ring boss and the third ring boss gets through the second top surface and the second bottom surface, a diameter of the first ring boss is smaller than a diameter of the second ring boss, the diameter of the second ring boss is smaller than a diameter of the third ring boss, the diameter of the third ring boss is smaller than a diameter of the third hole, wherein the cover is assembled on the bottom, the cover, the central body and the bottom is electrically insulated from each other;

the substrate defining three electrode points, the three electrode points comprises a first electrode point, a second electrode point and a third electrode point, wherein the three electrode points are insulated from each other, the first electrode point is electrically connected with the central body, the second electrode point is electrically connected with the bottom, the third electrode point is electrically connected with the cover.

2. The battery testing apparatus of claim 1, wherein the first hole, the second hole and the third hole are coaxial with the bottom.

3. The battery testing apparatus of claim 1, wherein the bottom defines a plurality of holes at the first side surface, the second step defines a plurality of air holes, an extending direction of the plurality of air holes is perpendicular to that of the plurality of holes, one of the plurality of air holes is communicated with one of the plurality of holes.

4. The battery testing apparatus of claim 3, wherein the plurality of holes is configured to connect two gas pipes to allow gas to enter and discharge.

5. The battery testing apparatus of claim 3, wherein the plurality of holes is sealed by a plurality of plugs.

6. The battery testing apparatus of claim 1, wherein the first ring boss, the second ring boss and the third ring boss are coaxial with the cover.

7. The battery testing apparatus of claim 1, wherein the second ring boss defines a plurality of grooves or one ring groove.

8. The battery testing apparatus of claim 1, wherein the cover further includes a quartz glass, the first ring boss defines a hollow space, the quartz glass is located in the hollow of the first ring boss.

9. The battery testing apparatus of claim 1, wherein the first top surface of the bottom defines a plurality of screw holes, the cover defines a plurality of counter bores.

10. The battery testing apparatus of claim 1, wherein further comprising a plurality of insulated bolts, wherein the plurality of insulated bolts are configured to fix the bottom, the central body and the cover.

11. The battery testing apparatus of claim 1, wherein a height of the first ring boss is smaller than a height of the second ring boss, the height of the second ring boss is smaller than a height of the third ring boss.

12. The battery testing apparatus of claim 1, wherein the first electrode point, the second electrode point and the third electrode point are electrically connected with three pins respectively, and the three pins are packaged to form a three-pin socket.

* * * * *